(12) United States Patent
McDaniel

(10) Patent No.: US 11,879,048 B2
(45) Date of Patent: Jan. 23, 2024

(54) ENZYMATIC SELF-CLEANING SEALANTS

(71) Applicant: REACTIVE SURFACES, LTD., LLP, Austin, TX (US)

(72) Inventor: Claude Steven McDaniel, Austin, TX (US)

(73) Assignee: REACTIVE SURFACES LTD., LLP, Austin, TX (US)

(*) Notice: Subject to any disclaimer, the term of this patent is extended or adjusted under 35 U.S.C. 154(b) by 331 days.

(21) Appl. No.: 17/167,053

(22) Filed: Feb. 3, 2021

(65) Prior Publication Data

US 2021/0238391 A1 Aug. 5, 2021

Related U.S. Application Data

(60) Provisional application No. 62/970,059, filed on Feb. 4, 2020.

(51) Int. Cl.
| | | |
|---|---|---|
| *C08K 13/02* | (2006.01) | |
| *C08L 33/04* | (2006.01) | |
| *C12N 9/20* | (2006.01) | |
| *C09D 7/60* | (2018.01) | |
| *C09D 5/34* | (2006.01) | |
| *C09K 3/10* | (2006.01) | |

(52) U.S. Cl.
CPC ............ *C08K 13/02* (2013.01); *C08L 33/04* (2013.01); *C09D 5/34* (2013.01); *C09D 7/60* (2018.01); *C12N 9/20* (2013.01); *C09K 3/1006* (2013.01)

(58) Field of Classification Search
CPC .......... C08K 13/02; C08L 33/04; C09D 5/34; C09D 7/60; C09K 3/1006; C12N 9/20
See application file for complete search history.

(56) References Cited

U.S. PATENT DOCUMENTS

2010/0233146 A1* 9/2010 McDaniel ............ C09D 5/1625
435/174

FOREIGN PATENT DOCUMENTS

EP 0587332 * 3/1994

OTHER PUBLICATIONS https://www.merriam-webster.com/thesaurus/caulk, "Caulk." Merriam-Webster.com Thesaurus, Merriam-Webster, https://www.merriam-webster.com/thesaurus/caulk. Accessed Jul. 30, 2023.*

* cited by examiner

*Primary Examiner* — Patrick D Niland
(74) *Attorney, Agent, or Firm* — Kilpatrick Townsend & Stockton LLP

(57) ABSTRACT

Sealants and caulks (i.e., polymeric fillers) disclosed herein are polymeric fillers that comprises a polymeric material composition and one or more lipolytic enzymes dispersed within the polymeric material composition. In preferred embodiments, the polymeric material composition is an acrylic latex sealant such as that in the form of a caulk and the one or more lipolytic enzymes comprises a lipase such as, preferably, a triacylglycerol lipase. Advantageously, the one or more lipolytic enzymes of such sealants and caulks degrades lipid-containing contaminants and resulting lipid-containing stains that contain lipids. The degradation is a result of the ability of a lipolytic enzyme to catalyze a reaction on a lipid-containing substance (i.e., a substrate) to hydrolyze or move (e.g., intra-esterification) ester bonds of such lipid-containing substance. This lipid-degradation functionality at least partially inhibits the growth of such mold and mildew resulting from exposure to lipid-containing contaminants.

10 Claims, No Drawings

ENZYMATIC SELF-CLEANING SEALANTS

CROSS-REFERENCE TO RELATED APPLICATIONS

This application claims priority to U.S. Provisional Application No. 62/970,059 filed Feb. 4, 2020, the contents of which are incorporated herein by reference in their entirety.

FIELD OF THE INVENTION

The invention relates generally to sealant such as caulk and, more specifically, to sealants and caulks comprising a lipolytic enzyme that degrades lipid-containing residues and stains in contact with such upon contact therewith.

BACKGROUND

It is well known that sealants of various types are used for forming a fluid-resistant interface between surfaces of adjacent structures. In many applications, the fluid is water, air or a combination thereof. The sealant is applied between the surfaces of the adjacent structures (e.g., edges thereof) such that the sealant fills a space between the adjacent structures and adheres to the surfaces defining such space, thereby preventing or limiting the ability of fluid to freely flow through the space. Such fluids may be liquid or gaseous.

Caulk is a specific type of sealant commonly used to provide a fluid-resistant interface between adjacent edges of building materials such as tiles, walls, wall boards, shower and bath enclosures and the like. Preferably, caulk has a hardness similar to the adjacent building materials. To this end, caulk generally exhibits relatively low elasticity and/or increased density relative some many other types of sealants. The term "polymeric filler" is used herein to jointly refer to sealants and caulks.

It is also well known that caulk is regularly used to form a fluid-resistant interface between building materials and structures in kitchen and bathrooms. For example, caulk is commonly used to provide a fluid-resistance interface between building materials bordering countertops and backsplashes and between building materials defining shower and bath enclosures. In these applications, the caulk routinely comes into contact with contaminants in the form of cooking matter (e.g., soiled water, oils and food juices), water contaminated by microorganisms from the human body, water contaminated by body oils produced by the human body, water contaminated by microorganisms in the water itself, water contaminated by hygiene products (e.g., soaps and the like), or a combination thereof. Additionally, the caulk can be exposed to contaminants in the form of air-borne microorganisms.

Over time, exposure to these contaminants often leads to stains resulting from the growth of mold and mildew. These stains are unsightly and lead to extensive cleaning to facilitate their removal. In many cases, such as when left unattended, these stains can require removal and replacement of the caulk to remediate these stains. Such remediation is both timely and costly. Therefore, sealants and caulks formulated to at least partially inhibit the growth of such mold and mildew resulting from exposure to such contaminants would be advantageous, desirable and useful.

SUMMARY OF THE INVENTION

Embodiments of the present invention are directed to sealants and caulks (i.e., polymeric fillers) comprising one or more lipolytic enzymes. Advantageously, the one or more lipolytic enzymes of such sealants and caulks degrades lipid-containing contaminants and resulting lipid-containing stains that contain lipids. The degradation is a result of the ability of a lipolytic enzyme to catalyze a reaction on a lipid-containing substance (i.e., a substrate) to hydrolyze or move (e.g., intra-esterification) ester bonds of such lipid-containing substance. This lipid-degradation functionality at least partially inhibits the growth of such mold and mildew resulting from exposure to lipid-containing contaminants.

The lipid-degradation functionality of sealants and caulks configured in accordance with one or more embodiments of the present invention completely or nearly completely inhibits the growth of such mold and mildew resulting from exposure to lipid-containing contaminants. Beneficially, inhibition of the growth of such mold and mildew resulting from the exposure to lipid-containing contaminants precludes the unsightly appearance of these stains (and contaminants) and promotes ease of cleaning (i.e., removal) of contaminants, thereby eliminating expensive and timely cleaning or remediation of affected sealants and caulks. In this regard, sealants and caulks configured in accordance with one or more embodiments of the present invention offer improved functionality relative to sealants and caulks that do not comprise one or more lipolytic enzymes.

In one or more embodiments, a polymeric filler comprises a polymeric material composition and one or more lipolytic enzymes dispersed within the polymeric material composition.

In one or more embodiments, the polymeric filler is one of a caulk and a sealant.

In one or more embodiments, the polymeric filler is an acrylic latex caulk.

In one or more embodiments, the polymeric material composition is an acrylic latex material composition.

In one or more embodiments, the polymeric material composition comprises an acrylic latex polymer.

In one or more embodiments, the polymeric filler comprises a filler/pigment, a petroleum distillate, and a glycol.

In one or more embodiments, the polymeric filler comprises one or more organic filler/pigment, one or more petroleum distillates and one or more glycol.

In one or more embodiments, the polymeric filler comprises a, aqueous acrylic emulsion polymer, a petroleum distillate, a coalescent, and a filler/pigment.

In one or more embodiments, the one or more filler/pigment include at least one of limestone, amorphous silica, quartz, carbon black, and titanium dioxide.

In one or more embodiments, the one or more lipolytic enzymes comprises one or more triacylglycerol lipase.

In one or more embodiments, the one or more lipolytic enzymes comprises at least one of a triacylglycerol lipase, a lipoprotein lipase, an acylglycerol lipase, a hormone-sensitive lipase, a galactolipase, a phospholipase, and a lysophospholipase.

In one or more embodiments, the one or more lipolytic enzymes comprises a phospholipase, wherein the phospholipase comprises at least one of a phospholipase $A_1$, phospholipases A, phospholipases C, phospholipases D, and phosphoinositide phospholipase C.

In one or more embodiments, preparing the polymeric filler comprises combining the constituent components of the polymeric material composition and thereafter dispersing the one or more lipolytic enzymes within the polymeric material composition.

In one or more embodiments, the polymeric filler comprises a plurality of lipolytic enzymes and preparing the polymeric filler comprises combining the plurality of lipolytic enzymes prior to dispersing the plurality of enzymes in the polymeric material composition.

These and other objects, embodiments, advantages and/or distinctions of the present invention will become readily apparent upon further review of the following specification, any associated drawings and any appended claims. Detailed descriptions of the embodiments are provided herein, as well as, the best mode of carrying out and employing the present invention. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

DETAILED DESCRIPTION OF THE INVENTION

Sealants refer to material compositions typically used to fill a joint to reduce or prevent passage of a gas (e.g., air), water, a small material (e.g., dust), a temperature change, or a combination thereof. A sealant coating ("sealant") may be thought of as a coating that bridges by contact two or more surfaces. A joint is a gap or opening between two or more surfaces, which may or may not be of the same material type (e.g., metal, wood, glass, masonry, plastic, etc). In typical embodiments, a joint has a width, depth, breadth, or a combination thereof, of 0.64 mm to 5.10 mm, including all intermediate ranges and combinations thereof. Examples of sealants (e.g., caulks, acrylics, elastomers, phenolic resin, epoxy, polyurethane, anaerobic and structural acrylic, high-temperature polymers, water-based industrial type adhesives, water-based paper and packaging adhesives, water-based coatings, hot melt adhesives, hot melt coatings for paper and plastic, epoxy adhesives, plastisol compounds, construction adhesives, flocking adhesives, industrial adhesives, general purpose adhesives, pressure sensitive adhesives, sealants, mastics, urethanes) for various surfaces (e.g., metal, plastic, textile, paper), adhesive and sealant components (e.g., antifoams, antioxidants, extenders, fillers, pigments, flame/fire retardants, oils, polymer emulsions, preservatives, bactericides, fungicides, resins, rheological/viscosity control agents, starches, waxes, acids, aluminum silicates, anti-skinning agents, calcium carbonates, catalysts, cross-linking agents, curing agents, clays, corn starch, starch derivatives, defoamers, antifoams, dispersing agents, emulsifying agents, epoxy resin diluents, lattices, polybutenes, polyvinyl acetates, preservatives, acrylic resins, epoxy resins, ester gums, ethylene/vinyl acetate resins, maleic resins, natural resins, phenolic resins, polyamide resins, polyethylene resins, polypropylene resins, polyterpene resins, powder coating resins, radiation coating resins, urethane resins, vinyl chloride resins, emulsion resins, dispersion resins, resin esters, rosins, silicas, silicon dioxide, stabilizers, surfactants/surface active agents, talcs, thickeners, thixotropic agents, waxes) techniques of preparation and assays for properties, have been described in Skeist, I., ed., *Handbook of Adhesives*, $3^{rd}$ Ed., Van Nostrand Reinhold, New York, 1990; Satriana, M. J. *Hot Melt Adhesives: Manufacture and Applications*, Noyes Data Corporation, New Jersey, 1974; Petrie, E. M., *Handbook of Adhesives and Sealants*, McGraw-Hill, New York, 2000; Hartshorn, S. R., ed., *Structural Adhesives—Chemistry and Technology*. Plenum Press, New York, 1986; Flick, E. W., *Adhesive and Sealant Compound Formulations*, $2^{nd}$ Ed., Noyes Publications, New Jersey, 1984; Flick, E., *Handbook of Raw Adhesives $2^{nd}$ Ed.*, Noyes Publications, New Jersey, 1989; Flick, E., *Handbook of Raw Adhesives*, Noyes Publications, New Jersey, 1982; Dunning, H. R., *Pressure Sensitive Adhesives—Formulations and Technology*, $2^{nd}$ Ed., Noyes Data Corporation, New Jersey, 1977; and Flick, E. W., Construction and Structural Adhesives and Sealants, Noyes Publications, New Jersey, 1988.

In certain embodiments, a sealant coating comprises an oil, a butyl, an acrylic, a blocked styrene, a polysulfide, a urethane, a silicone, or a combination thereof. A sealant may be a solvent-borne coating or a water-borne coating (e.g., a latex). In certain aspects, a sealant comprises a latex (e.g., an acrylic latex). In other embodiments, a sealant is selected for flexibility, as one or more of the joint surfaces may move during normal use. Examples of a flexible sealant include a silicone, a butyl, an acrylic, a blocked styrene, an acrylic latex, or a combination thereof. An oil sealant typically comprises a drying oil, an extender pigment, a thixotrope, and a drier. A solvent-borne butyl sealant typically comprises a polyisobytylene and/or a polybutene, an extender pigment (e.g., talc, calcium carbonate), a liquid component, and an additive (e.g., an adhesion promoter, an antioxidant, a thixotrope). A solvent-borne acrylic sealant typically comprises a polymethylacrylate (e.g., polyethyl, polybutyl), a colorant, a thixotrope, an additive, and a liquid component. A solvent-borne blocked styrene sealant typically comprises styrene, styrene-butadiene, isoprene, or a combination thereof, and a liquid component. A solvent-borne acrylic sealant, blocked styrene sealant, or a combination thereof typically is selected for aspects wherein UV resistance is desired. A urethane sealant may be a one-pack or two-pack coating. A solvent-borne one-pack urethane sealant typically comprises a urethane that comprises a hydroxyl moiety, a filler, a thixotrope, an additive, an adhesion promoter, and a liquid component. A solvent-borne two-pack urethane sealant typically comprises a polyether that comprises an isocyanate moiety in one-pack and a binder comprising a hydroxyl moiety in a second pack. A solvent-borne two-pack urethane sealant typically also comprises a filler, an adhesion promoter, an additive (e.g., a light stabilizer), or a combination thereof. In certain aspects, a solvent-borne urethane sealant is selected for a sealant with a good abrasion resistance. A polysulfide sealant may be a one-pack or two-pack coating. A solvent-borne one-pack polysulfide sealant typically comprises a urethane that comprises a hydroxyl moiety, a filler, a thixotrope, an additive, an adhesion promoter, and a liquid component. A solvent-borne two-pack polysulfide sealant typically comprises a first pack, which typically comprises a polysulfide, an opacifying pigment, a colorizer (e.g., a pigment), clay, a thixotrope (e.g., a mineral), and a liquid component; and a second pack, which typically comprises a curing agent (e.g., lead peroxide), an adhesion promoter, an extender pigment, and a light stabilizer. A silicone sealant typically comprises a polydimethyllsiloxane and a methyltriacetoxy silane, a methyltrimethoxysilane, a methyltricyclorhexylaminosilane, or a combination thereof. A water-borne acrylic latex sealant typically comprises a thermoplastic acrylic, a filler, a surfactant, a thixotrope, an additive, and a liquid component. Procedures for determining the suitability of a coating and/or film for use as a sealant coating have been described, for example, in "Paint and Coating Testing Manual, Fourteenth Edition of the Gardner-Sward Handbook," (Koleske, J. V. Ed.), pp. 735-740, 1995.

Sealants and caulks (i.e., polymeric fillers) formulated in accordance with embodiments of the present invention are a polymeric filler that comprises a polymeric material composition and one or more lipolytic enzymes dispersed within the polymeric material composition. In preferred embodiments, the polymeric filler is an acrylic latex sealant in the form of a caulk and the one or more lipolytic enzymes comprises a lipase such as, preferably, a triacylglycerol lipase. In one or more embodiments, the polymeric material composition is an acrylic latex material composition. Other lipolytic enzymes useful in sealants and caulks formulated in accordance with embodiments of the present invention include, but are not limited to, lipoprotein lipases, acylglycerol lipases, hormone-sensitive lipases, galactolipases, phospholipases, and lysophospholipases. The acrylic latex sealant can comprise an aqueous acrylic emulsion polymer, one or more fillers/pigments, a petroleum distillate, and one or more glycol. In some specific embodiments, the acrylic latex sealant comprises a coalescent. The one or more fillers/pigments include at least one of limestone, amorphous silica, quartz, carbon black, and titanium dioxide.

The one or more lipolytic enzymes of sealants and caulks formulated in accordance with embodiments of the present invention catalyze a reaction on a lipid-containing substance to hydrolyze or move (e.g., intra-esterification) ester bonds of such lipid-containing substance. Through such catalytic action, sealants and caulks formulated in accordance with embodiments of the present invention exhibit the novel and beneficial capability to degrade lipid-containing contaminants and resulting lipid-containing stains that contain lipids. Advantageously, the lipid-degradation functionality of sealants and caulks formulated in accordance with embodiments of the present invention completely or nearly completely inhibits the growth of such mold and mildew resulting from exposure to lipid-containing contaminants. Beneficially, inhibition of the growth of such mold and mildew resulting from the exposure to lipid-containing contaminants precludes the unsightly appearance of these stains (and contaminants) and promotes ease of cleaning (i.e., removal) of contaminants, thereby eliminating expensive and timely cleaning or remediation of affected sealants and caulks. In this regard, sealants and caulks configured in accordance with one or more embodiments of the present invention offer improved functionality relative to sealants and caulks that do not comprise one or more lipolytic enzymes.

Lipids

A cell wall may comprise a lipid, other than those described for a peptidoglycan, teichoic acid, or lipopolysaccharide. Typically, a cell comprises various lipid biomolecules, which generally comprise fatty acids. It is contemplated that in embodiments wherein a processing step comprises contacting the cell with a non-aqueous solvent, most lipids will be removed from the cell and/or or cell wall. However, it is contemplated that in embodiments wherein such a processing step does not occur, the lipid components of a cell and/or cell wall remaining in the particulate matter may affect coating or other surface treatment reactions wherein lipid (e.g., fatty acid double bond) cross-linking activity contributes to film-formation. Lipids of particular relevance for such potential cross-linking reactions include those of the outer membrane, which comprise fatty acids, the cell wall, or a combination thereof.

A lipid can be defined as a hydrophobic or amphipathic organic molecule extractable with a non-aqueous solvent, such as, for example, a triglyceride, a diglyceride, a monoglyceride, a phospholipid, a glycolipid (e.g., galactolipid), a steroid (e.g., cholesterol), a wax, a fat-soluble vitamin (e.g., vitamin A, D, E, K), a petroleum based material, such as, for example, a hydrocarbon composition such as gasoline, a crude petroleum oil, grease greases, etc., or an combination thereof. A lipid may comprise a combination (mixture) of lipids, such as a grease that comprises both a fatty acid-based lipid and a petroleum-based lipid. Some lipids are apolar (e.g., a hydrocarbons, a carotene), others are polar (e.g., triacylglycerol, a retinol, a wax, a sterol), and some polar lipids may have partial solubility in water (e.g., a lysophospholipid). Because of the prevalence of these types of lipids in activities such as, for example, restaurant food preparation and counterpart use in household applications, a coating and/or surface treatment will be formulated to comprise one or more lipolytic enzymes to promote lipid removal from surfaces contaminated with a lipid in these environments.

Lipolytic Enzymes

Enzymes are biomolecule that possesses the ability to accelerate a chemical reaction and comprises one or more chemical moieties typically synthesized in living organisms, including but not limited to, an amino acid, a nucleotide, a polysaccharide or simple sugar, a lipid, or a combination thereof. As used herein, the term "bioactive" or "active" refers to the ability of an enzyme to accelerate a chemical reaction differentiating such activity from a like ability of a composition, and/or a method that does not comprise an enzyme to accelerate a chemical reaction. In some embodiments, an enzyme can comprise a proteinaceous molecule. It is contemplated that any proteinaceous molecule that functions as an enzyme, whether identical to the wild-type amino acid sequence encoded by an isolated gene, a functional equivalent of such a sequence, or a combination thereof, may be used. As used herein, a "wild-type enzyme" refers to an amino acid sequence that functions as an enzyme and is identical to the sequence encoded by an isolated gene from a natural source. As used herein, a "functional equivalent" to the wild-type enzyme generally comprises a proteinaceous molecule comprising a sequence and/or a structural analog of a wild-type enzyme's sequence and/or structure and functions as an enzyme. The functional equivalent enzyme may possess similar or the same enzymatic properties, such as catalyzing chemical reactions of the wild-type enzyme's EC classification, or may possess other enzymatic properties, such as catalyzing the chemical reactions of an enzyme that is related to the wild-type enzyme by sequence and/or structure. An enzyme encompasses its functional equivalents that catalyze the reaction catalyzed by the wild-type form of the enzyme (e.g., the reaction used for EC Classification). For example, any functional equivalent of a lipase that retains lipase activity (e.g., catalyzes the reaction: triacylglycerol+$H_2O$=diacylglycerol+a carboxylate), though the activity may be altered (e.g., increased reaction rates, decreased reaction rates, altered substrate preference, etc.), is encompassed by the term "lipase" (i.e., in the claims, "lipase" encompasses such functional equivalents, "human lipase" encompasses functional equivalents of a wild-type human lipase, etc.). Examples of a functional equivalent of a wild-type enzyme are described herein and include mutations to a wild-type enzyme sequence, such as a sequence truncation, an amino acid substitution, an amino acid modification, a fusion protein, or a combination thereof, wherein the altered sequence functions as an enzyme. As used herein, the term "derived" or "obtained" refers to a biomolecule's (e.g., an enzyme) progenitor source, though the biomolecule may be wild-type or a functional equivalent of the original source biomolecule, and thus the term "derived" or "obtained" encompasses both wild-type and functional equivalents. For example, a coding sequence for a *Homo*

*sapiens* enzyme may be mutated and recombinantly expressed in bacteria, and the bacteria comprising the enzyme processed into a composition for use, but the enzyme, whether isolated or comprising other bacterial cellular materials, would be "derived" from *Homo sapiens*. In another example, a wild-type enzyme isolated from an endogenous biological source, such as, for example, a *Pseudomonas putida* lipase isolated from *Pseudomonas putida*, would be "derived" from *Pseudomonas putida*.

In certain embodiments, an enzyme may comprise a simple enzyme, a complex enzyme, or a combination thereof. As known herein, a "simple enzyme" is an enzyme wherein the chemical properties of moieties found in its amino acid sequence is sufficient for producing enzymatic activity. As known herein, a "complex enzyme" is an enzyme whose catalytic activity functions when an apo-enzyme is combined with a prosthetic group, a co-factor, or a combination thereof. An "apo-enzyme" is a proteinaceous molecule and is catalytically inactive without the prosthetic group and/or co-factor. As known herein, a "prosthetic group" or "co-enzyme" is non-proteinaceous molecule that is attached to the apo-enzyme to produce a catalytically active complex enzyme. As known herein, a "holo-enzyme" is a complex enzyme that comprises an apo-enzyme and a co-enzyme. As known herein, a "co-factor" is a molecule that acts in combination with the apo-enzyme to produce a catalytically active complex enzyme. A prosthetic group can be one or more bound metal atoms, a vitamin derivative, or a combination thereof. Examples of metal atoms that may be used as a prosthetic group and/or a co-factor include Ca, Cd, Co, Cu, Fe, Mg, Mn, Ni, Zn, or a combination thereof. Usually the metal atom is an ion, such as $Ca^{2+}$, $Cd^{2+}$, $Co^{2+}$, $Cu^{2+}$, $Fe^{+2}$, $Mg^{2+}$, $Mn^{2+}$, $Ni^{2+}$, $Zn^{2+}$, or a combination thereof. As known herein, a "metalloenzyme" is a complex enzyme that comprises an apo-enzyme and a prosthetic group, wherein the prosthetic group comprises a metal atom. As known herein, a "metal activated enzyme" is a complex enzyme that comprises an apo-enzyme and a co-factor, wherein the co-factor comprises a metal atom.

Enzymes are generally described by the classification system of The International Union of Biochemistry and Molecular Biology ("IUBMB"). The IUBMB classifies enzymes by the type of reaction catalyzed and enumerates each sub-class by a designated enzyme commission number ("EC"). Based on these broad categories, an enzyme may comprise an oxidoreductase (EC 1), a transferase (EC 2), a hydrolase (EC 3), a lyase (EC 4), an isomerase (EC 5), a ligase (EC 6), or a combination thereof. Often, an enzyme may be able to catalyze multiple reactions, and thus have multiple EC classifications.

Lipolytic enzyme generally comprises a hydrolase such as, for example, an esterase, a ceramidase (EC 3.5.1.23), or a combination thereof. Examples of an esterase is those identified by enzyme commission number (EC 3.1): a carboxylic ester hydrolase, (EC 3.1.3), a phosphoric monoester hydrolase (EC 3.1.3), a phosphoric diester hydrolase (EC 3.1.4), or a combination thereof. As used herein, a "carboxylic ester hydrolase" catalyzes the hydrolytic cleavage of an ester to produce an alcohol and a carboxylic acid anion product. As used herein, a "phosphoric monoester hydrolase" catalyzes the hydrolytic cleavage of an O—P ester bond. As used herein, a "phosphoric diester hydrolase" catalyzes the hydrolytic cleavage of a phosphate group's phosphorus atom and two other moieties over two ester bonds. As used herein a "ceramidase" hydrolyzes the N-acyl bond of ceramide to release a fatty acid and sphingosine. Examples of a lipolytic esterase and a ceramidase include a carboxylesterase (EC 3.1.1.1), a lipase (EC 3.1.1.3), a lipoprotein lipase (EC 3.1.1.34), an acylglycerol lipase (EC 3.1.1.23), a hormone-sensitive lipase (EC 3.1.1.79), a phospholipase $A_1$ (EC 3.1.1.32), a phospholipase $A_2$ (EC 3.1.1.4), a phosphatidylinositol deacylase (EC 3.1.1.52), a phospholipase C (EC 3.1.4.3), a phospholipase D (EC 3.1.4.4), a phosphoinositide phospholipase C (EC 3.1.4.11), a phosphatidate phosphatase (EC 3.1.3.4), a lysophospholipase (EC 3.1.1.5), a sterol esterase (EC 3.1.1.13), a galactolipase (EC 3.1.1.26), a sphingomyelin phosphodiesterase (EC 3.1.4.12), a sphingomyelin phosphodiesterase D (EC 3.1.4.41), a ceramidase (EC 3.5.1.23), a wax-ester hydrolase (EC 3.1.1.50), a fatty-acyl-ethyl-ester synthase (EC 3.1.1.67), a retinyl-palmitate esterase (EC 3.1.1.21), a 11-cis-retinyl-palmitate hydrolase (EC 3.1.1.63), an all-trans-retinyl-palmitate hydrolase (EC 3.1.1.64), a cutinase (EC 3.1.1.74), an acyloxyacyl hydrolase (EC 3.1.1.77), a petroleum lipolytic enzyme, or a combination thereof.

It is well known that lipolytic enzymes are generally classified as an alpha/beta fold hydrolase ("alpha/beta hydrolase"), due to a structural configuration generally comprising an 8-member beta pleated sheet, where many sheets are parallel, with several alpha helices on both sides of the sheet. A lipolytic enzyme's amino acid sequence commonly has Ser, Glu/Asp, His active site residues (e.g., Ser152, Asp176, and His263 by human pancreatic numbering). The Ser is comprised in a GXSXG substrate binding consensus sequence for many types of lipolytic enzymes, with a GGYSQGXA sequence being present in a cutinase. The active site serine is generally at a turn between a beta-strand and an alpha helix, and these lipolytic enzymes are classified as serine esterases. A substitution at the $1^{st}$ position Gly (e.g., Thr) has been identified in some lipolytic enzymes. Often a Pro residue is found at the residues 1 and 4 down from the Asp, and the His is typically within a CXHXR sequence. A lipolytic enzyme will generally have an alpha helix flap (a.k.a. "lid") region (around amino acid residues 240-260 by human pancreatic lipase numbering) covering the active site, with a conserved tryptophan in this region in proximity of the active site serine in many lipolytic enzymes [In "Advances in Protein Chemistry, Volume 45 Lipoproteins, Apolipoproteins, and Lipases." (Anfinsen, C. B., Edsall, J. T., Richards, Frederic, R. M., Eisenberg, D. S., and Schumaker, V. N. Eds.) Academic Press, Inc., San Diego, Calif., pp. 1-152, 1994; "Lipases their Structure, Biochemistry and Application" (Paul Woolley and Steffen B. Peterson, Eds.), pp. 1-243-270, 337-354, 1994.]. It is contemplated that all such alpha/beta hydrolases, particularly those possessing lipolytic activity, may be used in sealants and caulks formulated in accordance with embodiments of the present invention.

A lipolytic alpha/beta hydrolase's catalysis is usually dependent upon or stimulated by interfacial activation, which is the contact of a lipase with an interface where two layers of materials with differing hydrophobic/hydrophilic character meet, such as a water/oil interface of a micelle or emulsion, an air/water interface, or a solid carrier/organic solvent interface of an immobilized lipase. Interfacial activation is thought to result from lipid substrate forming an ordered confirmation in a localized hydrophobic environment, so that the substrate is more easily bound by a lipolytic enzyme than a lipid substrate's conformation in a hydrophilic environment. A conformational change in the flap region due to contact with the interface allows substrate binding in many alpha/beta hydrolases. Cutinase is lipolytic alpha/beta hydrolase that is not substantially enhanced by interfacial activation. The apparent difference in a cutinase is a lack of a lid, and the ability to bury the aliphatic FA chains in the active site cleft without the charge effects of an interface prompting a conformational change in the enzyme [In "Engineering of/with Lipases" (F. Xavier Malcata., Ed.), pp. 125-142, 1996].

In general embodiments, lipolytic enzymes contemplated for use hydrolyze esters of glycerol-based lipids (e.g., a triglyceride, a phospholipid). Glycerol is a naturally produced alcohol having a 3-carbon backbone with 3 alcohol moieties (positions 1, 2, and 3). One or more of these positions are often esterified with a fatty acid in many naturally produced or synthetic lipids. Common examples of triglycerides include a fat, which is solid at ambient conditions, or an oil, which is liquid at ambient conditions. As used herein, a "fatty acid" ("FA") refers to saturated, mono-unsaturated or polyunsaturated aliphatic acids. They may be "short chain" (2-6 carbons), "medium chain" (8-14 carbons) or "long chain" (16 or more carbons, e.g., 40 carbons) aliphatic acids. Lipolytic enzymes hydrolyze esters at one or more of glycerol's alcohol positions (e.g., a 1, 3 lipase), though lipolytic enzymes often can hydrolyze non-glycerol esters of an alcohol other than glycerol. For example, naturally produced waxes are fatty acid esters of ethylene glycol, which has a 2-carbon backbone and 2 alcohol moieties, where one or both of the alcohol moieties are esterified with a fatty acid.

Lipases are lipolytic enzymes catalyzes a reaction or series of reactions on a lipid substrate that produces one or more products that are more aqueous soluble, absorb easier into a coating or film, or an effective combination thereof, than the lipid substrate. In some embodiments, the enzyme catalyzes hydrolysis of a fatty acid bond, usually an ester bond. In other embodiments, the products produced are a free fatty acid, an alcohol moiety comprising product, or a combination thereof. In preferred embodiments, at least one product of catalytic activity of a lipolytic enzyme is soluble in an aqueous media such as water that may comprise detergent. To this end, such catalytic activity is conferred upon a sealant or caulk by incorporation (e.g., dispersion) therein.

Lipase (EC 3.1.1.3), which is a preferred lipolytic enzyme in sealants and caulks formulated in accordance with embodiment of the present invention, has been also referred to in that art as "triacylglycerol acylhydrolase," "triacylglycerol lipase," "triglyceride lipase," "tributyrase," "butyrinase," "glycerol ester hydrolase," "tributyrinase," "Tween hydrolase," "steapsin," "triacetinase," "tributyrin esterase," "Tweenase," "amno N-AP," "Takedo 1969-4-9," "Meito MY 30," "Tweenesterase," "GA 56," "capalase L," "triglyceride hydrolase," "triolein hydrolase," "tween-hydrolyzing esterase," "amano CE," "cacordase," "triglyceridase," "triacylglycerol ester hydrolase," "amano P," "amano AP," "PPL," "glycerol-ester hydrolase," "GEH," "meito Sangyo OF lipase," "hepatic lipase," "lipazin," "post-heparin plasma protamine-resistant lipase," "salt-resistant post-heparin lipase," "heparin releasable hepatic lipase," "amano CES," "amano B," "tributyrase," "triglyceride lipase," "liver lipase," and "hepatic monoacylglycerol acyltransferase." Lipase catalyzes the reaction: triacylglycerol+ $H_2O$=diacylglycerol+a carboxylate. In many embodiments, the carboxylate comprises a fatty acid. Lipase and/or co-lipase producing cells and methods for isolating a lipase and/or a co-lipase from cellular materials and biological sources have been described, [see, for example, Korn, E. D. and Quigley., 1957; Lynn, W. S. and Perryman, N.C., 1960; Tani, T. and Tominaga, Y. J., 1991; Sugihara, A. et al., 1992; in "Methods and Molecular Biology, Volume 109 Lipase and Phospholipase Protocols." (Mark Doolittle and Karen Reue, Eds.), pp. 157-164, 1999; pancreatic lipase via recombinant expression in a baculoviral system in "Methods and Molecular Biology, Volume 109 Lipase and Phospholipase Protocols." (Mark Doolittle and Karen Reue, Eds.), pp. 187-213, 1999; In "Lipases their Structure, Biochemistry and Application" (Paul Woolley and Steffen B. Peterson, Eds.), pp. 243-270, 1994; Brockerhoff, Hans and Jensen, Robert G. "Lipolytic Enzymes," 1974; "Lipases" (Borgstrom, B. and Brockman, H. L., Eds), p. 49-262, 307-328, 365-416, 1984; In "Lipases and Phospholipases in Drug Development from Biochemistry to Molecular Pharmacology." (Müller, G. and Petry, S. Eds.) pp. 1-22, 2004]. In contrast, a lipolytic enzyme classified as a carboxylesterase prefers short or medium chain FAs, though some carboxylesterases can also hydrolyze esters of longer FAs. The chain length preference for lipase is generally applicable to the other preferred lipolytic FA esterases and ceramidase described herein, other than carboxylesterases unless otherwise noted.

Enzyme Incorporation

Lipolytic enzymes of sealants and caulks formulated in accordance with embodiment of the present invention are incorporated into a polymeric material composition thereof. Such incorporation is implemented in a manner that enables the lipolytic enzyme to maintain enzymatic activity after such incorporation. Lipid-degradation functionality of sealants and caulks configured in accordance with one or more embodiments of the present invention is maintained to provide for complete or nearly complete inhibition of growth of such mold and mildew on such sealants and caulks resulting from exposure to lipid-containing contaminants thereon. To this end, lipolytic enzymes of sealants and caulks formulated in accordance with embodiment of the present invention can be incorporated into the polymeric material composition thereof through a number of different techniques.

Enzyme incorporation techniques include, but are not limited to, mechanical dispersion, encapsulation and immobilization. Mechanic dispersion involves the simple process of using energy delivered by a mechanical mixing device to combine the lipolytic enzymes into a polymeric material composition. Factors such as mixing time, rate of mixing, size of mixing device and the like influence the degree of homogeneity of the enzyme within the polymeric material composition. Mechanic dispersion is a preferred technique of enzyme incorporation for producing sealants and caulks formulated in accordance with embodiment of the present invention. Microencapsulation entails encapsulating an enzyme using a microencapsulation technique. Such encapsulation may enhance or confer the particulate nature of the biomolecular composition, provide protection to the biomolecular composition, increase the average particle size to a desired range, allow release of a cellular component (e.g., a biomolecule) from the encapsulating material, alter surface charge, hydrophobicity, hydrophilicity, solubility and/or dispersability of the particulate material, or a combination thereof. Examples of microencapsulation (e.g., microsphere) compositions and techniques are described in Wang, H. T. et al., J. of Controlled Release 17:23-25, 1991; and U.S. Pat. Nos. 4,324,683, 4,839,046, 4,988,623, 5,026,650, 5,153,131, 6,485,983, 5,627,021 and 6,020,312. Immobilization refers to attachment (e.g., by covalent or non-covalent interactions) of an enzyme to a solid support ("carrier") or crosslinking enzymes (e.g., CLEC). A carrier can be a component of a sealant or caulk (e.g., silica particles, carbon black, particles, titanium dioxide particles or the like). Methods of immobilization include, for example, absorption, ionic binding, covalent attachment, or cross-linking, entrapment into a gel, entrapment into a membrane compartment, or a combination thereof (Kurt Faber, "Biotransformations in Organic Chemistry, a Textbook, Third Edition." pp. 345-356, 1997). Immobilization of an enzyme provides the benefits of limiting conformational changes in the presence of solvents that result in loss of activity, preventing enzyme aggregation, improving enzyme resistance to proteolytic digestion by limiting conformational changes and exposure of cleavage sites, and to increasing the surface area of an exposed enzyme to a substrate for catalytic activity [In "Engineering of/with Lipases" (F. Xavier Malcata., Ed.) pp. 457-458, 1996; "Methods in non-aqueous enzymology" (Gupta, M. N., Ed.) p. 37, 2000]. Moreover, immobilization of an enzyme may be used to improve stability against oxidation (e.g., autooxidation) solvent, solute, or shear force denaturation, or self-digestion; prevent loss of enzymes by dissolving into water or other solvents and being washed away, and providing an increased concentration of enzyme in a local area for highest yield of products. Often other properties such a selectivity, pH and temperature optimums, Km, etc. may be altered by immobilization. Various types of substrates for enzyme immobilization include reverse micelles, zeolite, Celite Hyflo Supercel, anion exchange resin, Celite® (diatomaceous earth), polyurethane foam particles, macroporous polypropylene Accurel® EP 100, macroporous anionic resin beads, polypropylene membrane, acrylic membrane, nylon membrane, cellulose ester membrane, polyvinylidene difuoride membrane, filter paper, Teflon membrane, reverse micelles, ceramic membrane, macroporous packing particulate, polyamide, cellulose hollow fiber, resin or carrier, polypropylene membrane pretreated with a blocked copolymer, immunoglobins via enzyme-linked immunosorbent assay, agarose, ion-exchange resin, sol-gel (In "Engineering of/with Lipases" (F. Xavier Malcata., Ed.) pp. 298, 408, 409, 414, 422, 447, 448, 451, 461, 494, 501, 516, 546, 549, 1996; U.S. Pat. No. 4,939,090; Lopez, M. et al., 1998; "Methods in non-aqueous enzymology" (Gupta, M. N., Ed.) pp. 41-51, 63-65, 2000]. For example, a lipase incorporated in sol-gel had 100-fold improved activity (Reetz, M. et al., 1995).

Absorption may be used to attach an enzyme onto a material where it is held by non-covalent (e.g., hydrogen bonding, Van der Waals forces) interactions. Examples of materials that may be used for absorption of an enzyme include a woodchip, an activated charcoal, an aluminum oxide, a diatomaceous earth (e.g., Celite), a cellulose material, a controlled pore glass, a siliconized glass bead, or a combination thereof. In some cases, the buffering capacity of an immobilization carrier, such as diatomaceous earth (e.g., Celite), can improve the catalytic rate or selectivity of a lipolytic enzyme (e.g., Pseudomonas sp. lipase), as acids produced by ester hydrolysis can alter local pH to detrimentally effect the reaction (Kurt Faber, "Biotransformations in Organic Chemistry, a Textbook, Third Edition.", p. 114-115, 1997; "Lipases" (Borgstrom, B. and Brockman, H. L., Eds), p. 196, 1984]

Ion exchange resins, such as cation (e.g., carboxymethyl cellulose, Amberlite IRA), anion (e.g., sephadex, diethyl-aminoethylcellulose), or a combination thereof, may be used to immobilize an enzyme. Covalent bonding immobilization generally involves chemical reactions on an amino acid residue at an amino moiety (e.g., lysine's epsilon amino group), a phenolic moiety, a suflhydryl moiety, a hydroxyl moiety, a carboxy moiety, or a combination thereof, usually with a spacer chemical that is used to bind to the enzyme to a carrier. Examples of carriers that may be used to immobilize an enzyme by covalent bonds include porous glass via a spacer (e.g., an aminoalkylethoxy-chlorosilane, an aminoalkyl-chlorosilane); a polysaccharide polymer carrier (e.g., agarose, chitin, cellulose, dextran, starch) via reaction cyanogens bromide reactions; a synthetic co-polymer (e.g., polyvinyl acetate) via epichlorohydrin activation reactions; an epoxy-activate resin; a cation exchange resin activated to covalently bond by acid chloride conversion of carboxylic acids, or a combination thereof. Cross-linking enzymes may interconnect an enzyme to a like or different enzyme, sometimes with a filler protein (e.g., an albumin) separating the enzyme molecules, via a biofunctional agent (e.g., a glutardialdehyde, dimethyl adipimidate, dimethyl suberimidate and hexamethylenediisocyanate). Gel entrapment includes incorporation of enzymes or cells into gel matrices (e.g., an alginate, a carragenan gel, a polyacrylamide gel, or a combination thereof) that can be formed into various shapes (Karube, I. et al., 1985; Qureshi, N. et al., 1985; Umemura, I. et al., 1984; Fukui, S. and Tanaka, A. 1984; Mori, T. et al., 1972; Martinek, K. et al., 1977; Kurt Faber, "Biotransformations in Organic Chemistry, a Textbook, Third Edition." pp. 350-352, 1997). Membrane entrapment refers to restricting the space an enzyme functions in by being placed in a compartment, often imitating the separation of an enzyme that occurs inside a living cell (e.g., localization of an enzyme inside an organelle). Examples of membrane entrapment compositions include a micelle, a reversed micelle, a vesicle (e.g., a liposome), a synthetic membrane (e.g., a polyamide, a polyethersulfone) with a pore size smaller than the enzyme sequestering an enzyme (e.g., a membrane enclosed enzymatic catalysis or "MEEC"). However, a MEEC may reduce the function of many lipolytic enzymes, possibly due to interference with the interfacial activation process by this type of environment (Kurt Faber, "Biotransformations in Organic Chemistry, a Textbook, Third Edition." pp. 345-356, 1997).

Determining the Properties of Incorporated Enzymes

Sealants and caulk configured in accordance with embodiments of the present invention can be formulated to exhibit a desired set of properties for a particular use. To this end, such sealants and caulks may be formulated to achieve specific properties by varying the ranges and/or combinations of coating components. A variety of assays are available to measure desired properties (e.g., bioactivity) of sealant r caulk to determine the degree of suitability of such sealant or caulk for use in a particular use (see, for example, in "Hess's Paint Film Defects: Their Causes and Cure," 1979). It is contemplated that sealants and caulks configured in accordance with embodiments of the present invention may be subjected to one or more of such assays. As used herein, "bioactivity" refers to desired property such as color, enzymatic activity, etc, conferred to a sealant or caulk by an enzyme (i.e., a biomolecular composition). As used herein, "bioactivity resistance" refers to the ability of a biomolecular composition to confer a desired property during and/or after contact with a stress condition normally assayed for in a standard coating and/or film assay procedure. Examples of such a stress condition includes, for example, a temperature (e.g., a baking condition), contact with a coating component (e.g., an organic liquid component), contact with a chemical reaction (e.g., thermosetting film formation), contact with coating and/or film damaging agent (e.g., weathering, detergents, solvents), etc. In specific facets, wherein a biomolecular composition comprises a desired biomolecule, a biomolecule may possess a greater bioactivity resistance such as determined with standard assay procedure.

It is contemplated that such bioactivity resistance may be determined using a standard procedure for a coating and/or film described herein or in the art, in light of the present disclosures. In an example, any assay described herein or in the art in light of the present disclosures may be used to determine the bioactivity resistance wherein an enzyme retains detectable enzymatic activity upon contact with a condition typically encountered in a standard assay. Additionally, in certain aspects, it is contemplated that a coating and/or film comprising an enzyme may lose part of all of a detectable, desirable bioactivity during the period of time of contact with standard assay condition but regain part or all of the enzymatic bioactivity after return to non-assay conditions. An example of this process is the thermal denaturation of an enzyme at an elevated temperature range into a configuration with lowered or absent bioactivity, followed by refolding of an enzyme, upon return to a more suitable temperature range for the enzyme, into a configuration possessing part or all of the enzymatic bioactivity detectable prior to contact with the elevated temperature. In another example, an enzyme may demonstrate such an increase in bioactivity upon removal of a solvent, chemical, etc.

Techniques for measuring enzymatic degradation, specificity (e.g., positional specificity) for various lipids comprising an ester or other hydrolysable moiety, including a triglyceride such as triolein, olive oil, or tributyrin; chromogenic substrates such as 4-methylumbelliferone, or 4-methylumbelliferone; or radioactively labeled glycerol ester substrates, such as glycerol [$^3$H]oleic acid esters; are known to those of skill in the art (see, for example, Brockerhoff, Hans and Jensen, Robert G. "Lipolytic Enzymes." pp-25-34, 1974). To measure lipolytic enzyme activity against substrates, molecular monolayers of lipid substrates may be used to control variables such as pressure, charge potential, density, interfacial characteristics, enzyme binding, the effects of an inhibitor, in measuring lipolytic enzyme kinetics [see for example, Gargouri, Y. et al., 1989; Melo, E. P. et al., 1995; In "Methods and Molecular Biology, Volume 109 Lipase and Phospholipase Protocols." (Mark Doolittle and Karen Reue, Eds.), pp 279-302, 1999].

Measuring the activity, stability, and other properties of lipolytic enzymes are known to those of skill in the art. For example, methods for measuring the activity of phospholipase $A_2$ and phospholipase C by the thin layer chromatography product separation, the fluorescence change of labeled substrates (e.g., dansyl-labeled glycerol, pyrene-PI, pyrene-PG), the release of products from radiolabled substrates (e.g., [$^3$H]Plasmenylcholine) have been described [see for example, in "Methods and Molecular Biology, Volume 109 Lipase and Phospholipase Protocols." (Mark Doolittle and Karen Reue, Eds.), pp. 1-17, 31-48, 1999]. Similarly, the release of fluorogenic products from substrates such as, for example, 1-trinitrophenyl-aminododecanoyl-2-pyrenedecanoyl-3-O-hexadecyl-sn-glycerol, or radioactive products from radiolabled substrates such as, for example, [$^3$H] triolein; glycerol tri[9,10(n)-[$^3$H]oleate; cholesterol-[$1^{24}$C]-oleate; 1(3)-mono-[$^3$H]oleoyl-2-O-mono-oleyleglycerol (a.k.a. [$^3$H]-MOME) and 1(3)-mono-oleoyl-2-O-mono-oleylglycerol (a.k.a. MOME); by lipolytic enzymes that catalyze hydrolysis of tri, di, or monoacylglycerols and sterol esters may be used to measure such enzymes' activity [see for example, in "Methods and Molecular Biology, Volume 109 Lipase and Phospholipase Protocols." (Mark Doolittle and Karen Reue, Eds.), pp. 18-30, 59-121, 1999]. Other assays using radiolabeled E. coli membranes to measure phospholipase activity in comparison to photometric and other assays has also been described [In "Esterases, Lipases, and Phospholipases from Structure to Clinical Significance." (Mackness, M. I. and Clerc, M., Eds.), pp 263-272, 1994].

As used herein other than the claims, the terms "a," "an," "the," and "said" means one or more. As used herein in the claim(s), when used in conjunction with the words "comprises" or "comprising," the words "a," "an," "the," or "said" may mean one or more than one. As used herein "another" may mean at least a second or more. As used in the claims, "about" refers to any inherent measurement error or a rounding of digits for a measured or calculated value (e.g., ratio), and thus the term "about" may be used with any value or range. Various genera and sub-genera described herein are contemplated both as individual components, as well as and mixtures and combinations that may be described in the claims as "at least one selected from," "a mixture thereof" and/or "a combination thereof." For example, compositions described as a coating suitable for plastic surfaces described in different sections of the specification may be claimed individually or as a combination, as they are part of the same genera of plastic coatings. All patents and publications mentioned in this specification are herein incorporated by reference to the same extent as if each individual publication was specifically and individually indicated to be incorporated by reference.

SUMMARY OF THE DETAILED DESCRIPTION

In some embodiments, the average weight per single particle ("primary particle") of a biomolecular composition (e.g., a lipolytic enzyme) may be measured in "wet weight," which refers to the weight of the particle prior to a drying or an extraction step that would remove the liquid component of a cell (e.g., the aqueous component of the cell's cytoplasm). In certain aspects, the "wet weight" of a biomolecular composition (e.g., a whole cell particulate material) that has its liquid component replaced by some other liquid (e.g., an organic solvent) may also be measured in "wet weight." The "dry weight" refers to the average per particle weight of a biomolecular composition after the majority of the liquid component has been removed. The term "majority" refers 50% to 100%, including all intermediate ranges and combinations thereof, with the greater values (e.g., 85% to 100%) contemplated. In general embodiments, it is contemplated that the dry weight of a biomolecular composition will typically be 5% to 30% the wet weight, including all intermediate ranges and combinations thereof, as it is usual for 70% to 95% of a cell to be water. Any technique for measuring cell or particle size, volume, density, etc. used for various insoluble particulate materials (e.g., pigments) used as coating, paint, or surface treatment components may be applied to a biomolecular composition to determine wet or dry weight values, particle size, particle density, etc. Additionally, various examples of specific techniques are described herein. Further, such measurements of cell size, shape, density, numbers, etc. is used in the art of microbiology. For example, the average number of particles, size, shape, etc. of a biomolecular composition may be microscopically determined for a given volume and weight of material, whether prepared as a "wet weight" or "dry weight material," and the average particle weight, density, volume, etc. calculated.

Many variations of nomenclature are commonly used to refer to a specific chemical composition. Accordingly, several common alternative names may be provided herein in quotations and parentheses/brackets, or other grammatical technique, adjacent to a chemical composition's preferred designation when referred to herein. Additionally, many chemical compositions referred to herein are further identified by a Chemical Abstracts Service registration number. The Chemical Abstracts Service provides a unique numeric designation, denoted herein as "CAS No.," for specific chemicals and some chemical mixtures, which unambiguously identifies a chemical composition's molecular structure.

It is contemplated that one of skill in the art may readily modify these types of techniques by replacement of a purified or immobilized enzyme typically assayed with compositions such as, for example, a biomolecular composition, a coating, a surface treatment, to assay and characterize the enzymatic activity of such a composition. Such measurements of the enzymatic activity of compositions may be used to select formulations with the desired activity properties of stability, activity, and such like, in different environmental conditions (e.g., pressure, interfacial characteristics, the effects of an inhibitor, temperature, detergent, organic solvent, etc.) or after contact with different substrates (e.g., contact with substrates mimicking vegetable oil properties vs. those for a sterol) to assess properties such as the substrate preference, enantiomeric specificity, kinetic properties, etc. of a composition.

One skilled in the art will readily appreciate that the present invention is well adapted to carry out and obtain the ends and features mentioned as well as those inherent therein. It should be understood, however, that the biomolecular compositions, compounds, coatings, paints, films, methods, procedures, and techniques described herein are presently representative of various embodiments. These techniques are intended to be exemplary, are given by way of illustration only, and are not intended as limitations on the scope. Other features will be readily apparent to one skilled in the art from the following detailed description; specific examples and claims; and various changes, substitutions, other uses and modifications that may be made to the invention disclosed herein without departing from the scope and spirit of the invention or as defined by the scope of the appended claims.

WORKING EXAMPLES

Example 1: Lipases in Sealant Activity at Different Concentrations

Sealant Composition #1, typically used in caulk applications (Table 1), was mixed (typically by hand with a stir rod) at 3.0, 0.5, and 0.25 wt % (based on solids) with various lipases (Table 2) and cured as sealant pellets and/or sealant strips.

TABLE 1

Sealant Composition #1 (Acrylic Latex Caulk)

| CAS No. | Material | Amount |
|---|---|---|
| 1317-65-3 | Limestone | 40%-50% |
| 64742-54-7 | Distillates, petroleum, hydrotreated heavy paraffinic | 1%-5% |
| 107-21-1 | Ethylene glycol | 1%-5% |
| 13463-67-7 | Titanium dioxide | 0.5%-1.5% |
| 9016-45-9 | Poly(oxy-1,2-ethanediyl), .alpha.-(nonylphenyl)-.omega.-hydroxy- | 0.5%-1.5% |
| 10605-21-7 | Carbamic acid, 1H-benzimidazol-2-yl-, methyl ester | 0.1%-1.0% |

TABLE 2

Lipases

| Lipase | Composition | Supplier |
|---|---|---|
| Lipase NL-GXT granulate | Lipase encapsulated in cellulosic matrix with a titanium dioxide coating: <5% Lipase (CAS No. 9001-62-1), derived from genetically modified *Aspergillus* spp., enzymatically active pH 7-12 (optimum pH 11), and active between 10° C.-70° C. (optimum 35° C.); <7% Titanium dioxide (CAS No. 13463-67-7) | Enzyme Supplies Limited, John Eccles House, The Oxford Science Park, Oxford OX4 4GP, United Kingdom ("Enzyme Supplies") |
| Lipase 100 | Lipase (CAS No. 9001-62-1) | Silver Fern Chemical, Inc, 2226 Queen Ann Ave N./Seattle, Washington 98109 U.S.A. ("Silverfern") |
| Lipase 100,000 | *Aspergillus niger* lipase (CAS No. 9001-62-1) and maltodextrin carrier: enzymatically active pH 3-12 (optimum pH 9), and active between 10° C.-70° C. (optimum about 35° C.); | American Biosystems, 345 Luck Avenue Roanoke, Virginia 24016 U.S.A. ("American Biosystems") |
| Lipase AN | *Aspergillus niger* lipase, food grade comprising 30% glycerol, 60% water and 10% lipase (CAS No. 9001-62-1): enzymatically active pH 7-12 (optimum pH 7), and active between about 20° C.-90° C. (optimum about 50° C.) | Creative Enzymes, 45-1 Ramsey Road Shirley, New York 11967, U.S.A. ("Creative Enzymes"; Catalog No. DI-1028) |
| Lipase 200,000 FIP/g | *Candida cylindracea* (*rugosa*) lipase: 8%-13% by weight lipase (CAS No. 9001-62-1), enzymatically active pH 3-10 (optimum pH 10), and active between about 20° C.-70° C. (optimum about 45° C.); 47%-64% by weight potato dextrin (CAS No. 9004-53-9); Remainder is maltodextrin (Waxy Maize) (CAS No. 9050-36-6) | BIO-CAT, Inc., 9117 Three Notch Road, Troy, Virginia 22974 U.S.A. ("BioCat") |

The cured sealant-lipase formulations were maintained at room temperature. Hydrolysis activity was measured using a spot colorimetric assay, wherein the lipase hydrolyzes the ester bond of the triglyceride mimic, 4-nitrophenyl acetate, to produce a yellow compound, 4-nitrophenol that has an extinction coefficient of 18000 $M^{-1}$ $cm^{-1}$ at 405 nm. A 4-nitrophenyl acetate spot assay for the sealant formulations was conducted by preparing Tris-HCl Buffer (7.2 pH) in deionized $H_2O$, and a stock solution of 200 mM 4-nitrophenyl acetate in 99% pure acetonitrile. Sealant pellets (approximate 1 $cm^2$ pellets) were put onto a plastic sheet in that were cured overnight at room temperature (approximately 20° C.). The sealant pellets were placed in wells of a 96 well plate being gently rocked, and 15 µL of 2.9 mM 4-nitrophenyl acetate created by dilution with deionized $H_2O$ and 15 µL of 7.2 pH Tris Buffer were added to each well. Sealant strips had 4-nitrophenyl acetate assay liquid applied to each strip's surface. After 15 minutes, 20 µL of each assay solution were placed into a 384-well plate and the absorbance measured at 405 nm. Pellet free wells were used to measure non-enzymatic hydrolysis of 4-nitrophenyl acetate to subtract from the pellet measurements to produce an adjusted absorbance value. Each assay of sealant-lipase formulation was done in triplicate. The adjusted absorbance value used in Beer's law (Absorbance=concentration in moles per liter times the pathlength in centimeters times the extinction coefficient) to determine the µM of 4-nitrophenol/minute created by lipase hydrolysis activity. Each sealant-lipase formulation was assayed 4 times for activity at day 0, 2 weeks, and 2 months (about 8 weeks) after cure. The lipases' average activity the 4 assays at each time of testing, and some of the standard deviations (in brackets), are shown at Table 3. An activity of about 8 µM/min/$cm^2$ desired for some applications of self-cleaning activity.

TABLE 3

Lipases' Activity in Sealant Composition #1

| Lipase | Time (Weeks) | Lipase Hydrolysis Activity mM/minute | | |
|---|---|---|---|---|
| | | 3.0 wt % | 0.5 wt % | 0.25 wt % |
| Lipase NL-GXT granulate (Enzyme Supplies) | 0 | 28.0 (1.0) | 22.2 (4.2) | 19.1 (2.4) |
| | 2 | 28.2 | 27.4 | 21.8 |
| | 8 | 28.9 | 28.6 | 23.4 |
| Lipase 100 (Silverfern) | 0 | 24.0 (4.5) | 18.0 (6.9) | 10.2 (3.9) |
| | 2 | 29.8 | 24.2 | 15.7 |
| | 8 | 27.1 | 26.7 | 16.8 |
| Lipase 100,000 (American Biosystems) | 0 | 31.2 (6.5) | 19.8 (3.9) | 17.2 (4.2) |
| | 2 | 32.0 | 25.2 | 36.7 |
| | 8 | 25.5 | 23.8 | 23.9 |
| Lipase AN (Creative Enzymes) | 0 | 32.6 (2.6) | 26.5 (4.5) | 22.4 (3.9) |
| | 2 | 24.7 | 29.0 | 22.4 |
| | 8 | 34.7 | 31.8 | 38.7 |
| Lipase 200,000 FIP/g (BioCat) | 0 | 30.5 (8.0) | 15.9 (6.7) | 15.2 (2.6) |
| | 2 | 23.7 | 17.7 | 19.1 |
| | 8 | 28.7 | 23.1 | 22.5 |

Most of the lipase functionalized sealant formulations retained their activity levels (within error) from over 2 weeks, with the Lipase 100,000 (American Biosystems) sealant at 0.25 wt % loading showing a significant increase in activity at the 2 week point. The activities for each of lipase sealant formulation were not statistically different from each other at the 0.5 wt % loading level. At 2 months, there was no significant loss of lipase activity, and in some sealant formulations lipase activity increased.

Example 2: Lipases in Sealant Thermal Stability

Cartridges of Sealant Composition #1 comprising various lipases (see Table 4) at different concentrations were prepared. Samples of each sealant formulation had 4-nitrophenyl acetate assay liquid applied to their surface and measured for lipase activity (day 0). The sealant-lipase formulations were stored in a 48.9° C. oven, a 35° C. oven, and at room temperature and samples assayed again after 2 and 4 weeks (see Table 4).

TABLE 4

Various Lipases' Hydrolysis Activity mM/minute after Incubation in Sealant Composition #1 at Different Temperatures

| Lipase | Activity Day 0 | Activity at 2 Weeks | | | Activity at 4 Weeks | |
|---|---|---|---|---|---|---|
| | | 20° C. | 35° C. | 48.9° C. | 20° C. | 35° C. |
| 0.5 wt % of total formulation Lipase NL-GXT granulate (Enzyme Supplies) | 15.5 ± 2.2 | 12.4 ± 2.1 | 13.7 ± 0.8 | None | 14.2 ± 0.8 | 11.9 ± 1.0 |
| 0.38 wt % of total formulation (0.5 wt % of solids) Lipase NL-GXT granulate (Enzyme Supplies) | 14.5 ± 2.0 | 12.3 ± 1.2 | 13.5 ± 2.2 | None | 18.9 ± 1.3 | 11.4 ± 1.4 |
| 0.5 wt % of total formulation Lipase 100 (Silverfern) | 16.4 ± 2.4 | 13.8 ± 2.0 | 15.2 ± 0.9 | None | 18.3 ± 1.4 | 15.1 ± 1.6 |
| 0.5 wt % of total formulation Lipase 100,000 (American Biosystems) | 15.5 ± 3.7 | 13.4 ± 3.4 | 14.9 ± 0.4 | None | 15.8 ± 0.7 | 9.2 ± 1.6 |

The thermal stability of several lipases in Sealant Composition #1 was further evaluated by preparing and sealing syringes containing functionalized sealant and storing the syringes in an oven at temperatures of 35° C., 37.8° C., 40.6° C., 43.3° C., 46.1° C., and 48.9° C. for 24 hours. The sealant formulations were coated onto a plastic substrate and allowed to dry overnight before testing for hydrolysis activity using the 4-nitrophenyl acetate spot assay method. The sealant formulations and thermal stability measurements are shown in Table 5. The sealant-lipase formulations all experienced a drop in activity at 48.9° C. after 24 hours, though they were all still active.

solids). The hydrolysis activity of the sealant formulations were measured in triplicate at the time of syringe loading (day 0) at room temperature, and at 1 day, 2 days, 5 days, 14 days, and 28 days of exposure to 48.9° C. Each sealant formulation was smeared with a putty knife onto a paperboard substrate and allowed to cure at room temperature overnight before being measured for enzyme activity using the 4-nitrophenylacetate spot assay. The activity and standard deviation are provided below in Table 7.

TABLE 5

Various Lipases' Hydrolysis Activity mM/minute after Incubation in Sealant Composition #1 at Different Temperatures

| Lipase | 35° C. | 37.8° C. | 40.6° C. | 43.3° C. | 46.1° C. | 48.9° C. |
|---|---|---|---|---|---|---|
| 0.5 wt % of total formulation Lipase NL-GXT granulate (Enzyme Supplies) | 19.3 ± 1.4 | 18.2 ± 1.4 | 17.6 ± 0.9 | 18.6 ± 0.4 | 17.9 ± 3.5 | 13.6 ± 1.1 |
| 0.38 wt % of total formulation (0.5 wt % of solids) Lipase NL-GXT granulate (Enzyme Supplies) | 17.9 ± 0.4 | 17.9 ± 0.6 | 18.4 ± 0.5 | 18.2 ± 1 | 17.4 ± 0.3 | 14 ± 0.6 |
| 0.5 wt % of total formulation Lipase NL-GXT granulate (Enzyme Supplies) | 15.9 ± 0.8 | 15.5 ± 2.2 | 15.6 ± 1.8 | 16.6 ± 0.5 | 16.9 ± 0.6 | 14.4 ± 4.5 |

Example 3: Thermal Stability of Lipases in Sealants

Sealant Composition #1 off-gases at 48.9° C. and the lipase loses activity in the sealant at that temperature over time. To further evaluate lipase thermal stability in sealant, the Sealant Composition #1 and an additional sealant (listed at Table 6; also used as a caulk) were mixed with various concentrations of different lipases. All lipase concentrations were wt % of the total formulation weight (not percent

TABLE 6

Sealant Composition #2 (Acrylic Latex Caulk) Composition

| CAS No. | Material | Amount |
|---|---|---|
| 1317-65-3 | Limestone | 20%-30% |
| 64742-54-7 | Distillates, petroleum, hydrotreated heavy paraffinic | 5%-10% |
| 107-21-1 | Ethylene glycol | 1%-5% |
| 13463-67-7 | Titanium dioxide | 1%-5% |
| 127087-87-0 | Poly(oxy-1,2-ethanediyl), .alpha.-(4-nonylphenyl)-.omega.-hydroxy-, branched | 1%-2% |

TABLE 7

Lipase Sealant Hydrolysis Activity after Storage at 48.9° C.

| | Activity in 15-minute test [uM/min (Standard Deviation)] | | | | | |
|---|---|---|---|---|---|---|
| Sealant Formulation | Day 0 | 1 Day | 2 Day | 5 Day | 14 Day | 28 Day |
| 0.5% Lipase NL-GXT granulate (Enzyme Supplies)/Sealant Composition #1 | 13.2 (1.5) | 10.6 (1.9) | 2.5 (0.5) | 2.7 (1.9) | 0.7 (4.7) | 1.8 (1.5) |
| 0.5% Lipase NL-GXT granulate (Enzyme Supplies)/Sealant Composition #1 | 17.6 (3.1) | 12.1 (2.9) | 6.8 (2.6) | 3.8 (1.1) | 0.5 (0.5) | 2.3 (2.2) |
| 1.5% Lipase NL-GXT granulate (Enzyme Supplies)/Sealant Composition #1 | 17.5 (1.3) | 14.2 (1.3) | 11.0 (3.2) | 11.6 (1.7) | 5.8 (0.4) | 3.9 (0.3) |
| 3.0% Lipase NL-GXT granulate (Enzyme Supplies)/Sealant Composition #1 | 12.8 (2.3) | 18.8 (1.0) | 18.1 (2.0) | 16.5 (1.9) | 17.6 (1.8) | 13.9 (2.2) |
| 0.5% Lipase NL-GXT granulate (Enzyme Supplies)/Sealant Composition #2 | 18.2 (3.4) | 10.4 (2.0) | 13.8 (0.8) | 8.6 (1.7) | 4.5 (0.7) | 3.0 (0.4) |

TABLE 7-continued

Lipase Sealant Hydrolysis Activity after Storage at 48.9° C.

| Sealant Formulation | Activity in 15-minute test [uM/min (Standard Deviation)] | | | | | |
|---|---|---|---|---|---|---|
| | Day 0 | 1 Day | 2 Day | 5 Day | 14 Day | 28 Day |
| 1.5% Lipase NL-GXT granulate (Enzyme Supplies)/Sealant Composition #2 | 14.9 (0.8) | 13.2 (1.2) | 12.1 (1.4) | 9.9 (0.2) | 9.8 (1.4) | 4.7 (0.9) |
| 3.0% Lipase NL-GXT granulate (Enzyme Supplies)/Sealant Composition #2 | 16.5 (4.8) | 17.2 (2.9) | 14.0 (1.4) | 15.9 (1.9) | 13.4 (2.0) | 11.9 (0.5) |
| 0.5% Lipase 100 (Silverfern)/Sealant Composition #1 | 17.6 (4.7) | 8.7 (1.2) | 5.4 (1.0) | 2.6 (0.8) | 6.2 (0.7) | 3.7 (0.8) |
| 0.5% Lipase 100 (Silverfern)/Sealant Composition #1 | 18.6 (4.0) | 11.2 (3.2) | 7.8 (1.1) | 4.8 (1.9) | 2.2 (0.6) | −0.4 (0.7) |
| 1.5% Lipase 100 (Silverfern)/Sealant Composition #1 | 19.2 (1.9) | 14.5 (4.2) | 10.7 (1.9) | 12.1 (0.6) | 4.2 (0.4) | 0.3 (1.2) |
| 3.0% Lipase 100 (Silverfern)/Sealant Composition #1 | 20.0 (2.6) | 18.0 (2.3) | 16.5 (1.6) | 13.8 (2.4) | 9.0 (0.7) | 5.5 (1.2) |

Example 4: Sealants with Lipase Activity and Water Sensitivity

Various sealants (Table 8, each typically used as a caulk) were evaluated for lipase hydrolysis activity and water sensitivity of each sealant, when formulated with and without lipase. Water sensitivity was evaluated by two measures, the first being rubbing with a wet finger upon a sealant formulation at various times after cure initiation to see if any white material from the sealant was removed. Removal of sealant material indicated the curing process was not yet completed. The second water sensitivity assay, after cure initiation, was visual evaluation of differences in appearance (e.g., bubbling, blistering) after water immersion of half of a draw-down layer of sealant formulation relative to the half of the sealant layer that was not water immersed.

TABLE 8

Sealant Compositions Nos. 3-8 (Acrylic Latex Caulks)

| Sealant | CAS No. | Material | Amount |
|---|---|---|---|
| Sealant Composition #3 (DAP Alex) | 1317-65-3 | Limestone | 50%-75% |
| | 64741-88-4 | Petroleum distillates | 2.5%-10% |
| | 120-55-8 | Diethylene glycol dibenzoate | 1.0%-2.5% |
| | 64741-89-5 | Solvent ref. light paraffinic | 1.0%-2.5% |
| | 27138-31-4 | Dipropylene glycol dibenzoate | 1.0%-2.5% |
| | 14808-60-7 | Quartz | 0.1%-1.0% |
| | 13463-67-7 | Titanium dioxide | 0.1%-1.0% |
| Sealant Composition #4 (DAP Alex Fast Dry) | 1317-65-3 | Limestone | 50%-75% |
| | 64741-88-4 | Petroleum distillates | 1.0%-2.5% |
| | 120-55-8 | Diethylene glycol dibenzoate | 1.0%-2.5% |
| | 14808-60-7 | Quartz | 0.1%-1.0% |
| | 13463-67-7 | Titanium dioxide | 0.1%-1.0% |
| Sealant Composition #5 (DAP Dynaflex 230) | 1317-65-3 | Limestone | 25%-50% |
| | 120-55-8 | Diethylene glycol dibenzoate | 2.5%-10% |
| | 20587-61-5 | Diethylene glycol monobenzoate | 1.0%-2.5% |
| | 13463-67-7 | Titanium dioxide | 1.0%-2.5% |
| | 107-21-1 | Ethylene glycol | 1.0%-2.5% |
| | 7631-86-9 | Amorphous silica | 1.0%-2.5% |
| | 1333-86-4 | Carbon black | 0.1%-1.0% |
| | 14808-60-7 | Quartz | 0.1%-1.0% |
| Sealant Composition #6 (DAP Alex Flex) | 1317-65-3 | Limestone | 25%-50% |
| | 64741-88-4 | Petroleum distillates | 2.5%-10% |
| | 120-55-8 | Diethylene glycol dibenzoate | 2.5%-10% |
| | 20587-61-5 | Diethylene glycol monobenzoate | 1.0%-2.5% |
| | 13463-67-7 | Titanium dioxide | 1.0%-2.5% |
| | 64741-89-5 | Solvent ref. light paraffinic | 1.0%-2.5% |
| | 14808-60-7 | Quartz | 0.1%-1.0% |
| Sealant Composition #7 (DAP KwikSeal Ultra) | N/A | Aqueous Acrylic Emulsion Polymer | 50%-75% |
| | 8042-47-5 | White mineral oil | 1.0%-2.5% |
| | 25265-77-4 | Texanol | 1.0%-2.5% |
| | 13463-67-7 | Titanium dioxide | 1.0%-2.5% |
| Sealant Composition #8 (DAP Alex Plus) | 1317-65-3 | Limestone | 45%-70% |
| | 72623-86-0 | Lubricating petroleum oil | 3%-7% |
| | 64741-88-4 | Petroleum distillates | 1%-5% |
| | 27138-31-4 | Dipropylene glycol dibenzoate | 1%-5% |
| | 64741-89-5 | Solvent ref. light paraffinic | 0.5%-1.5% |
| | 120-55-8 | Diethylene glycol dibenzoate | 0.5%-1.5% |
| | 14808-60-7 | Quartz | 0.1%-1.0% |
| | 13463-67-7 | Titanium dioxide | 0.1%-1.0% |
| | 1333-86-4 | Carbon black | 0.1%-1.0% |

Generally sealant in the form of acrylic latex caulks comprise an acrylic polymer, often siliconized, and typically as a latex dispersion or emulsion of the polymer particles in water, with a filler such as calcium carbonate or titanium dioxide, and a solids weight between about 58% to about 82%. For example, Sealant Composition #3 (DAP Alex) has a solids weight of nominally 82%, Sealant Composition #4 (DAP Alex Fast Dry) has a solids weight of nominally 82%, Sealant Composition #5 (DAP Dynaflex 230) has a solids weight of nominally 78%, Sealant Composition #6 (DAP Alex Flex) has a solids weight of nominally 80%, Sealant Composition #7 (DAP KwikSeal Ultra) has a solids weight of nominally 60%, and Sealant Composition #8 (DAP Alex Plus) has a solids weight of nominally 75%. Further formulation composition and preparation details are provided in European Patent Application Publication No. 0587332A1, European Patent Application Publication No. 0220851A1, U.S. Pat. No. 4,340,524A, which are all incorporated herein in their entirety.

Each sealant was weighed in a dish and 0.005 times that weight (0.5 wt % of total formulation) lipase powder (Lipase 100,000, American Biosystems) was added to the dish. The lipase was stirred into the sealants using a wooden tongue depressor until it was visually well mixed. Sealants without added lipase was used as controls. Each sealant-lipase formulation was coated onto a 3×6" bright white ceramic tile at 3/16" thickness and left to cure at room temperature and humidity for 48±2 hours and 72±2 hours.

Each sealant-lipase formulation was evaluated for lipase activity using a 4-nitrophenyl acetate spot assay. Stock assay solutions of 200 mM 4-nitrophenylacetate in acetonitrile and 200 mM TRIS/HCl buffer at 7.2 pH were prepared. Diluted enzyme substrate (2.9 mM 4-nitrophenyl acetate) was prepared from the stock solution of 200 mM by diluting in freshly collected deionized water. Onto each sealant-lipase formulation was dispensed 20 μl of TRIS/HCl buffer in triplicate and 20 μl of TRIS/HCl buffer was also dispensed onto a clean plastic surface in triplicate as a blank. Then, 20 μl of the 2.9 mM 4-nitrophenyl acetate solution was added to each spot on the sealant-lipase formulations and the blank spots. After 15 minutes, 20 μl was removed from each spot and transferred to a 384-well plate. The absorbance was read at 405 nm and using the pathlength of the plate and Beer's law, the concentration over time (0/l/min) of 4-nitrophenol generated was calculated.

Each sealant-lipase formulation panel was evaluated for water sensitivity by wetting a finger in tap water and rubbing the same horizontal pathway across the sealant drawdown 10 times in a back-and-forth motion (one back-and-forth pathway=1 double rub). After the 10 double rubs, the finger and the sealant-lipase formulation were examined for a milky white appearance of the water indicating removal of some of the surface of the sealant composition. If the water was still clear, this was noted as a "no"; if the water was milky in appearance, this was noted as a "yes". Each sealant-lipase formulation on a panel was also evaluated for water sensitivity by being placed in a plastic container containing room temperature tap water at a level to cover approximately the bottom half of the panel. After soaking for 2 hours, the panels were removed from the water and immediately photographed to visually evaluate any bubbling/blistering or other defects caused by the soaking process to the sealant-lipase formation. The results for the lipase activity and water sensitivity assays are shown in Table 9.

TABLE 9

Lipase Activity Evaluation and Water Sensitivity of Various Sealants

| Sealant | Hydrolysis Activity | | Wet Finger Double Rub | | Water Soak | |
| --- | --- | --- | --- | --- | --- | --- |
| | 48 Hour Cure Activity (μM/min) | 72 Hour Cure | 48 Hour Cure Milky (Yes/No) | 72 Hour Cure | 48 Hour Cure Bubbling/Swelling (Yes/No) | 72 Hour Cure |
| Sealant Composition #1 | −0.1 ± 0.6 | 2.5 ± 2.9 | No | No | No | No |
| Sealant Composition #1 + 0.5 wt % lipase | 30.7 ± 3.3 | 38.6 ± 6.8 | No | No | Yes | Yes, slight |
| Sealant Composition #3 | 4.1 ± 3.1 | 1.4 ± 0.5 | Yes, slight | Yes, slight | Yes | Yes |
| Sealant Composition #3 + 0.5 wt % lipase | 48.5 ± 2.2 | 36.9 ± 11.3 | Yes, slight | Yes, slight | Yes | Yes |
| Sealant Composition #4 | 3.2 ± 1.5 | 2.0 ± 1.0 | No | Yes, slight | Yes | Yes |
| Sealant Composition #4 + 0.5 wt % lipase | 38.4 ± 1.5 | 51.7 ± 4.6 | Yes | Yes, slight | Yes | Yes |
| Sealant Composition #5 | −0.6 ± 1.3 | −0.7 ± 0.5 | No | No | No | No |
| Sealant Composition #5 + 0.5% wt % lipase | 20.2 ± 1.2 | 25.3 ± 1.6 | No | No | No | No |
| Sealant Composition #6 | 1.9 ± 1.2 | 2.4 ± 0.9 | No | Yes, slight | Yes, slight | Yes, slight |
| Sealant Composition #6 + 0.5% wt % lipase | 33.0 ± 6.9 | 42.4 ± 2.3 | Yes | Yes | Yes, slight | Yes, slight |
| Sealant Composition #7 | 7.5 ± 3.9 | 4.0 ± 2.4 | No | No | No | No |
| Sealant Composition #7 + 0.5% wt % lipase | 19.2 ± 9.0 | 34.0 ± 9.7 | No | No | Yes, slight | No |
| Sealant Composition #8 | Soaked drops | Soaked drops | Yes | Yes | Yes | Yes |
| Sealant Composition #8 + 0.5% wt % lipase | Soaked drops | Soaked drops | Yes | Yes | Yes | Yes |

What is claimed is:

1. A self-cleaning caulk, comprising:
   an acrylic latex caulk having a solids weight of at least 75%; and
   one or more lipolytic enzymes dispersed within the caulk, wherein the one or more lipolytic enzymes are present at a concentration of not greater than 0.5% by solids weight.

2. The self-cleaning caulk of claim 1, wherein the one or more lipolytic enzymes dispersed within the caulk consists of triacylglycerol lipase.

3. The self-cleaning caulk of claim 1, wherein the caulk comprises a filler/pigment, a petroleum distillate, and a glycol.

4. The self-cleaning caulk of claim 1, wherein the caulk comprises one or more organic filler/pigment, one or more petroleum distillates, and one or more glycol.

5. The self-cleaning caulk of claim 1, wherein the caulk comprises an aqueous acrylic emulsion polymer, a petroleum distillate, a coalescent, and a filler/pigment.

6. The self-cleaning caulk of claim 5, wherein the one or more lipolytic enzymes comprises one or more triacylglycerol lipase.

7. The self-cleaning caulk of claim 6, wherein the caulk includes at least one of limestone, amorphous silica, quartz, carbon black, and titanium dioxide.

8. The self-cleaning caulk of claim 1, wherein the one or more lipolytic enzymes comprises one or more triacylglycerol lipase.

9. The self-cleaning caulk of claim 1, wherein the one or more lipolytic enzymes comprises at least one of a triacylglycerol lipase, a lipoprotein lipase, an acylglycerol lipase, a hormone-sensitive lipase, a galactolipase, a phospholipase, and a lysophospholipase.

10. The self-cleaning caulk of claim 1, wherein the one or more lipolytic enzymes comprises a phospholipase, wherein the phospholipase comprises at least one of a phospholipase $A_1$, phospholipases A, phospholipases C, phospholipases D, and phosphoinositide phospholipase C.

* * * * *